(12) United States Patent
Längle et al.

(10) Patent No.: US 12,274,425 B2
(45) Date of Patent: Apr. 15, 2025

(54) SURGICAL INSTRUMENT AND LOCKING DEVICE THEREOF

(71) Applicant: KARL STORZ SE & Co. KG, Tuttlingen (DE)

(72) Inventors: Dominik Längle, Tuttlingen (DE); Janosz Schneider, Tuttlingen (DE); Jochen Stefan, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 412 days.

(21) Appl. No.: 17/869,890

(22) Filed: Jul. 21, 2022

(65) Prior Publication Data
US 2023/0033865 A1 Feb. 2, 2023

(30) Foreign Application Priority Data
Jul. 28, 2021 (DE) .................... 10 2021 119 531.4

(51) Int. Cl.
*A61B 17/00* (2006.01)
(52) U.S. Cl.
CPC .............. *A61B 17/00234* (2013.01); *A61B 2017/00384* (2013.01)
(58) Field of Classification Search
CPC ........ A61B 17/0401; A61B 2017/0464; A61B 2017/0496; A61B 17/00234; A61B 2017/00384; A61B 34/71; A61B 2017/292; A61B 17/29; A61B 34/30
See application file for complete search history.

(56) References Cited

U.S. PATENT DOCUMENTS

| | | | |
|---|---|---|---|
| 5,456,683 A * | 10/1995 | Fritzsch | A61B 18/1442 606/41 |
| 9,526,495 B2 * | 12/2016 | Martin | A61B 17/0625 |
| 2013/0304041 A1 | 11/2013 | Merz et al. | |
| 2013/0310813 A1 * | 11/2013 | Kaercher | A61B 17/00234 403/321 |

FOREIGN PATENT DOCUMENTS

| | | |
|---|---|---|
| DE | 102012007650 A1 | 10/2013 |
| EP | 0565049 A1 | 10/1993 |

OTHER PUBLICATIONS

Office Action for corresponding German Patent Application No. 10 2021 119 531.4, mailed Apr. 19, 2022, 6 pages.

* cited by examiner

*Primary Examiner* — Kelly J Bekker
*Assistant Examiner* — Andrew P. Restaino
(74) *Attorney, Agent, or Firm* — Jason H. Vick; AMPED IP LLC (57) ABSTRACT

A locking device arranged in an actuation unit of a surgical instrument which has a hollow shaft with the actuation unit arranged at a proximal end of the shaft and having a tool at the distal end of the shaft which can be actuated by an instrument insert which can be movably stored axially in the direction of a main instrument axis (A) in the shaft. The locking device has an engagement element and an actuation device with which the engagement element can be transferred from a release position into a locking position. The engagement element can be a locking bolt which longitudinal axis runs perpendicular to the main axis (A) of the instrument and which has an engagement section configured for engagement with the instrument insert at a first end and a guide section. The locking bolt can be moved in two directions of movement by the actuation device.

10 Claims, 6 Drawing Sheets

SURGICAL INSTRUMENT AND LOCKING DEVICE THEREOF

CROSS-REFERENCE TO RELATED APPLICATIONS

This application claims the benefit under 35 U.S.C. 119(a) to German Patent Application No. 10 2021 119 531.4, filed 28 Jul. 2021, the disclosure of which is incorporated herein by reference in its entirety.

BACKGROUND

An exemplary embodiment relates to a surgical instrument and a locking device in order to fix and release a tool mechanism on the instrument tip of the surgical instrument.

Surgical instruments are known from the prior art, which can be guided manually or by a robot and have a hollow shaft, at the distal end of which the instrument tip is located with a tool, while at the proximal end of the shaft there is arranged a grip or an actuation unit for actuation of the tool. The tool can be, for example, a gripping or cutting tool with at least two jawing elements, the surgical instrument having an actuating mechanism for opening and closing the jawing elements, which usually comprises an instrument insert mounted axially in the shaft, which can be a rod element, e.g., a push/pull rod, which is in operative connection with the actuation unit on the proximal side and can be actuated by pulling and pushing to open and close the jawing elements on the instrument tip. E.g., to fix a specific position of the jawing elements of a gripping tool, surgical instruments can have a locking mechanism that is present in the handling and is formed by engagement with the instrument insert for releasing and fixing the tool mechanism on the distal instrument tip.

EP 0565049 A1 discloses a locking mechanism for a surgical instrument equipped with a grip for manual operation. The locking arrangement disposed in the grip is actuated by a trigger arrangement which is moved a first distance in a first direction to lock the tool mechanism to the distal end of a rod member by linear movement parallel to the rod member. In order to unlock or release the tool mechanism, the trigger arrangement is moved further a second distance in the first, i.e., the same, direction. A pivotable brake lever is provided as the engagement element with the rod element, which has an opening through which the rod element extends, the brake lever for locking when the trigger arrangement moves the first distance being pivoted under the influence of a return spring in such a way that the opening of the brake lever is eccentrically positioned with respect to the rod member and the frictional engagement thereby created inhibits movement of the rod member. By further moving the trigger the second distance in the same direction to unlock, a cam mechanism is activated in cooperation with a latch spring, whereupon the trigger, when released, is returned to the original position by a biasing spring, thereby pivoting the brake lever back so that the rod element again extends concentrically and thus unimpeded through the opening in the brake lever.

This locking device is operated manually and requires various springs within the hand grip, which limits its service life, since the springs lose their elasticity and thus their spring force after a certain period of use.

Based on this state of the art, one aspect of the present disclosure is to provide a locking device for releasing or fixing a tool mechanism for a surgical instrument, which can be actuated by a motor and is therefore suitable for use in a robot end effector, and on the other hand an increased duration of use or a non-changing constant response.

This object is achieved by a locking device having the features of claim 1.

The additional object of providing a surgical instrument that can be actuated by a robot, which has an improved locking device for releasing or fixing a tool mechanism, is solved by the surgical instrument having the features of independent claim 10.

Developments of the locking device and the surgical instrument are set out in the dependent claims.

According to a first embodiment of a locking device, this is provided for a surgical instrument which has a hollow shaft with an actuation unit arranged at a proximal end of the shaft and with a tool at the distal end of the shaft. The tool can be actuated by an instrument insert, which is mounted in the shaft so that it can move axially in the direction of a main instrument axis, which corresponds to the longitudinal axis of the shaft. The locking device is intended to be arranged in the actuation unit and has an engagement element for engagement with the instrument insert and an actuation device which is designed to move the engagement element from a release position in which there is no engagement with the instrument insert, so that it can be moved axially in a locking position in which the engaging member engages the instrument insert to prevent axial movement, and vice versa, from the locking position to the releasing position. According to one embodiment, the engagement element is a locking bolt which longitudinal axis runs perpendicular to the main instrument axis and which has an engagement section at a first end for engagement with the instrument insert and a guide section at a second end that is operatively connected to the actuation device. This has the advantageous effect that the locking bolt can be transferred from the release position to the locking position by the actuation device in a first direction of movement along the longitudinal axis of the locking bolt perpendicular to the main instrument axis, and vice versa in a second direction of movement opposite to the first direction of movement along the longitudinal axis of the locking bolt perpendicular to the main instrument axis from the locking position to the release position.

That is, the direction of movement of the locking bolt caused by the actuation device for transferring the locking bolt between the release position and the locking position always runs along the longitudinal axis of the locking bolt perpendicular to the main instrument axis, thereby advantageously enabling alternative motor drive options. Due to the linear back and forth movement of the locking bolt for locking and unlocking the instrument insert extending perpendicularly thereto, the number of spring elements required can also be reduced or dispensed with altogether.

"Instrument insert" is to be understood here as meaning all instrument inserts, such as a pull rod or pull/push rod, which are designed to be axially movable at the tip of the instrument in order to actuate a tool.

"Actuation device" means a transmission component—preferably driven or drivable by a motor—which transmits a drive movement such as the rotary movement of a motor into the linear reciprocating movement of the locking bolt and thus a linear movement of a train or train/push rod causes.

The definition of the first direction of movement for transferring the locking bolt from the release to the locking position and the second direction of movement for transferring the locking bolt from the locking to the release position is used here to distinguish between the opposite directions. The orientation of the first and second direction of movement towards or away from the instrument insert depends on the design of the engagement section of the locking bolt, i.e., in which direction an engagement takes place, which then represents the first direction of movement, as a result of which the second direction of movement for releasing the engagement is correspondingly opposite.

In a particularly preferred embodiment of the locking device, the actuation device is a cam wheel with a cam track that extends in an arc of a circle, i.e., with a constant radius, around an axis of rotation of the cam wheel between a first end stop and a second end stop. A depth of the cam track increases from the first end stop to the second end stop, so that a bottom of the cam track runs inclined between the first end stop and the second end stop. In an alternative embodiment, the cam track can also have a radius that can be changed along its course and thus have a snail shape. In this variant, too, the bottom of the cam track can be inclined.

The locking bolt is guided in the cam track, with the longitudinal axis of the locking bolt being parallel to the axis of rotation of the cam wheel. By guiding the locking bolt on the inclined bottom in the cam track, the locking bolt is only moved in the direction of movement along its longitudinal axis perpendicular to the main instrument axis between the release position and the locking position by rotating the cam wheel about its axis of rotation. This means that the first direction of movement of the locking bolt along its longitudinal axis perpendicular to the main instrument axis is provided by rotating the cam wheel in a first direction of rotation, and the second direction of movement of the locking bolt along the longitudinal axis of the locking bolt perpendicular to the main instrument axis is provided by rotating the cam wheel in a second direction of rotation opposite to the first direction of rotation. The direction of rotation causing a direction of movement of the locking bolt towards or away from the instrument insert depends on the direction of inclination of the cam track, i.e., whether the depth of the cam track increases clockwise or anticlockwise. The design of the cam track with a circular arc shape and gradient allows the locking bolt running in it to be moved back and forth, for example up and down, depending on the angular position of the cam wheel in its longitudinal direction for loosening and fixing the instrument insert. With this cam wheel as an actuation device, the rotation of a motor can advantageously be easily deflected into the linear actuating movement of the locking bolt, with a space-saving arrangement of the motor being made possible, e.g., in or preferably below an end effector on the robot system.

In a further advantageous embodiment of a locking device, the locking bolt and the cam wheel are arranged in such a way that the longitudinal axis of the locking bolt lies in the perpendicular direction, i.e., runs vertically, so that the directions of movement of the locking bolt lie in and against the direction of gravity. In the cam wheel, which is then arranged horizontally, the first end stop is an upper end stop with respect to the vertical direction and the second end stop is a lower end stop with respect to the vertical direction, so that the locking bolt arranged in the cam track parallel to the axis of rotation is moved from the lower end stop by the rotation of the cam wheel in one direction of rotation and can be raised to the upper end stop against the force of gravity, and can be lowered from the upper end stop under the force of gravity upon rotation of the cam wheel in the opposite direction of rotation to the lower end stop. In this preferred embodiment, no further components are advantageously required to hold the locking bolt from the upper end stop to the lower end stop at the bottom of the cam track, since this is done by gravity if the locking bolt has a sufficient weight.

Alternatively, however, it can also be provided in a further embodiment that the locking device has a fuse element which holds the guide section of the locking bolt on the bottom of the cam track independently of an orientation of the longitudinal axis of the locking bolt in relation to the plumb direction. The longitudinal axis of the locking bolt can then also be arranged deviating from the vertical direction if this appears to be more expedient for reasons of space. Different fuse elements are conceivable for this purpose, such as a restoring element which acts on the locking bolt with a restoring force in order to press the locking bolt against the bottom in the cam track.

With regard to the engagement of the locking bolt with the instrument insert, a further embodiment of the locking device provides that the instrument insert has a detached section as an engagement element with the locking bolt, which provides a distal-side axial contact surface and a proximal-side axial contact surface. The detached section can preferably be a detached head section at the proximal end of the instrument insert. Here, "distal side" refers to a contact surface that points in the distal direction on the distal side of the detached section, and "proximal side" refers to the contact surface that points in the proximal direction on the proximal side of the detached section. For this purpose, the detached section or the head section can have a rotationally symmetrical cross-sectional area that is larger than the cross-sectional area of the rest of the instrument insert, so that the detached section is delimited by two heels or the head section by one heel. Alternatively, a neck section can be provided between the detached section or the head section and the rest of the instrument insert (each), the cross-sectional area of which is smaller than that of the detached section or head section and the rest of the instrument insert, so that the detached section or head section that can be replaced by a heel is delimited from the neck section. The shape of the detached section or head section is limited to rotationally symmetrical shapes suitable for providing the distal-side and proximal-side contact surfaces, for example, the detached section or head section can be cylindrical with a circular or polygonal cross section or spherical.

For engagement with this detached section or head section, the locking bolt has a receiving bore on the engagement section, which extends perpendicularly to the longitudinal axis of the locking bolt and is dimensioned to accommodate the detached section or head section, wherein the receiving bore is oriented in the direction of the main instrument axis or parallel thereto. By way of example, "sized to receive" may mean that the bore cross-sectional area is in a range of 1.1 to 2.5 times the head cross-section. The locking device has a distal contact surface for the distal-side axial contact surface of the detached section and a proximal contact surface for the proximal-side axial contact surface of the detached section, with at least the distal contact surface adjoining the receiving bore in the direction of the longitudinal axis of the locking bolt. The distal counter-contact surface and the proximal counter-contact surface are spaced apart from one another by the length of the detached section in the direction of the main instrument axis, so that in the locking position the detached section of the instrument insert engages behind the receiving bore by the detached section with the distal-side and proximal-side axial contact surface between the distal and the proximal counter-contact surface which comes to rest. This prevents the instrument insert from moving axially in the distal and proximal directions.

In some embodiments, the receiving bore can be a through-bore, i.e., the receiving bore extends completely through the locking bolt, so that the distal counter-contact surface for the distal-side axial contact surface of the instrument insert is present on a proximal outer surface of the locking bolt. In this case, the proximal counter-contact surface for the proximal-side axial contact surface is provided by a separate component, which is arranged proximal to the proximal outer surface of the locking bolt. The instrument insert then extends through the receiving bore, so that the detached section or the head section of the instrument insert projects out of the receiving bore of the locking bolt on the proximal side. In the release position, in which the instrument insert can be moved axially to actuate the distal tool mechanism or for removal, the detached section or the head section is therefore within a spatial projection of the receiving bore parallel to the main instrument axis and can therefore move in and through the instrument insert in the axial direction and the mounting hole can be moved. For locking, the locking bolt is displaced along its longitudinal axis, so that the detached section or head section protruding from the receiving bore on the proximal side comes to rest between the distal counter-contact surface on the outer surface of the locking bolt and the proximal counter-contact surface on the separate component, so that an axial movement of the instrument insert is prevented. The directions of movement for locking and releasing depend on the position of the intended distal counter-contact surface in relation to the receiving bore, since two distal counter-contact surfaces ("above" and "below" the receiving bore in the case of a vertically arranged locking bolt) adjoin to the receiving bore in relation to the longitudinal axis of the locking bolt).

As an alternative to the embodiment with the distal counter-contact surface on the outer surface of the locking bolt and the separate component for the end contact surface, it can be provided in a preferred embodiment that the distal and the proximal counter-contact surfaces of the locking bolt are provided by an engagement bore, which is perpendicular to the receiving bore and parallel to or along the longitudinal axis of the locking bolt at least as far as the receiving bore, so that the distal and proximal counter-contact surfaces are present within the locking bolt and the detached section or head section of the instrument insert does not extend out of the locking bolt. In this embodiment the receiving bore can be a through-bore in order to be suitable both for an instrument insert with a detached head section and for an instrument insert with a detached section, which is not formed at the proximal end but in the proximal end section, which is inside the actuation unit of the surgical instrument.

In a preferred embodiment, which is provided for an instrument insert with a detached head section, the receiving bore can be a blind bore which extends to the engagement bore, so that a proximal wall of the engagement bore is adjacent to a proximal wall of the blind bore. The proximal counter-contact surface within the locking bolt is provided not only by the proximal wall of the engagement bore, but also by the proximal wall of the blind bore.

Because in the variants with an engagement bore, the head section is partially accommodated in the engagement bore in the locking position when the detached section or head section engages with the distal-side and proximal-side contact surfaces between the distal and proximal counter-contact surfaces, the engagement bore is suitable in shape and dimension adjusted to the detached section or head section. In the locking position after the locking bolt has been moved along its longitudinal axis, the detached section or head section protrudes into the engagement bore, so that the distal-side axial contact surface points to the distal counter-contact surface and the proximal-side axial contact surface to the proximal counter-contact surface, thereby preventing any axial movement of the instrument insert. By moving the locking bolt into the release position, in which the instrument insert can be moved axially to actuate the distal tool mechanism or also for removal, the detached section or head section completely enters the receiving bore. Here, too, the directions of movement for locking and releasing depend on the position of the distal and proximal counter-contact surface provided in relation to the receiving bore, if the engagement bore extends further than the receiving bore, since then at the receiving bore in relation to the longitudinal axis of the locking bolt two distal and two proximal counter-contact surfaces adjoin ("above" and "below" the mounting hole). In the event that the engagement bore extends only as far as the receiving bore, so that the distal counter-stop is formed only above the receiving bore for a locking bolt arranged vertically with the engagement section at the top, the locking bolt is moved downwards for locking so that the detached section or head section is fixed axially with the axial contact surfaces between the distal and proximal counter-contact surface. To release this locking bolt it is moved upwards along its longitudinal axis, so that the detached section or head section is completely in the receiving bore and thus allows an axial movement of the instrument insert.

In order to guide the actuating movement of the locking bolt, the locking device can have at least one guide element in a further embodiment, which provides a guide surface parallel to the longitudinal axis of the locking bolt for guiding the locking bolt along its longitudinal axis perpendicular to the main instrument axis. "Guide surface" here means a surface on which the indexing pin is slidably guided with an outer wall section; but this is not limited to a flat surface. The guide surface can also be provided only by a rail element parallel to the longitudinal axis of the locking bolt, or it can be a surface shaped to match the shape of the locking bolt. Alternatively, the locking bolt can have a flattened section in order to be guided by a guide element with a flat guide surface. The guide element can preferably be arranged on a housing component through which the instrument insert extends. Particularly and preferably, the guide element can be placed in relation to the locking bolt in such a way that an outer wall section on the engagement section of the locking bolt can be guided through the guide element. The position of the guide element, dimensions of the guide surface and/or dimensions of the locking bolt on the outer wall section to be guided can be designed in such a way that the locking bolt can be locked at any position along its path of movement, which is caused by the actuation device from the first, upper end stop to the second, lower end stop which is guided by the guide element.

In a further embodiment of the locking device, it can also be provided that the locking device provides a stop for a stop surface of the locking bolt, which extends perpendicularly to the longitudinal axis of the locking bolt, the stop being positioned in relation to the instrument insert in such a way that when the locking bolt rests the stop surface is present on the stop in the release position. This ensures that an exchangeable instrument insert can only be removed when the locking bolt is at the stop, i.e., in the release position.

In order to drive the actuation device designed as a cam wheel with a motor, in a further embodiment of the locking device, the cam wheel can have a drive ring section or a circumferential drive ring along a predetermined circumferential section, which is operatively connected to a drive element that can be driven by the motor. The drive ring can be, for example, a ring gear, with the drive element engaged therewith being a pinion. Alternatively, the drive ring and the drive element can be formed, for example, by traction pulleys that are operatively connected by a traction means.

An additional aspect is a surgical instrument which, in a first embodiment, has a hollow shaft with an actuation unit arranged at a proximal end of the shaft and with a tool at the distal end of the shaft. The distal tool can be actuated by an instrument insert, which is mounted in the shaft so that it can move axially in the direction of the main instrument axis, which corresponds to the longitudinal axis of the shaft. The surgical instrument has a locking device which is arranged in the actuation unit and has an engagement element for engagement with the instrument insert and an actuation device which is designed to move the engagement element from a release position, in which there is no engagement with the instrument insert and the axially movable instrument insert, to a locking position in which the engagement member engages the instrument insert to prevent axial movement, and vice versa. The locking device of the surgical instrument according to one embodiment is a locking device according to one embodiment.

BRIEF DESCRIPTION OF THE DRAWINGS

Further embodiments of the locking device, as well as some of the advantages associated with these and other embodiments, will become apparent and better understood from the following detailed description with reference to the accompanying figures. Items or parts thereof that are substantially the same or similar may be given the same reference numbers. The figures are only a schematic representation of an embodiment.
Showing.

DETAILED DESCRIPTION

Figure 1:
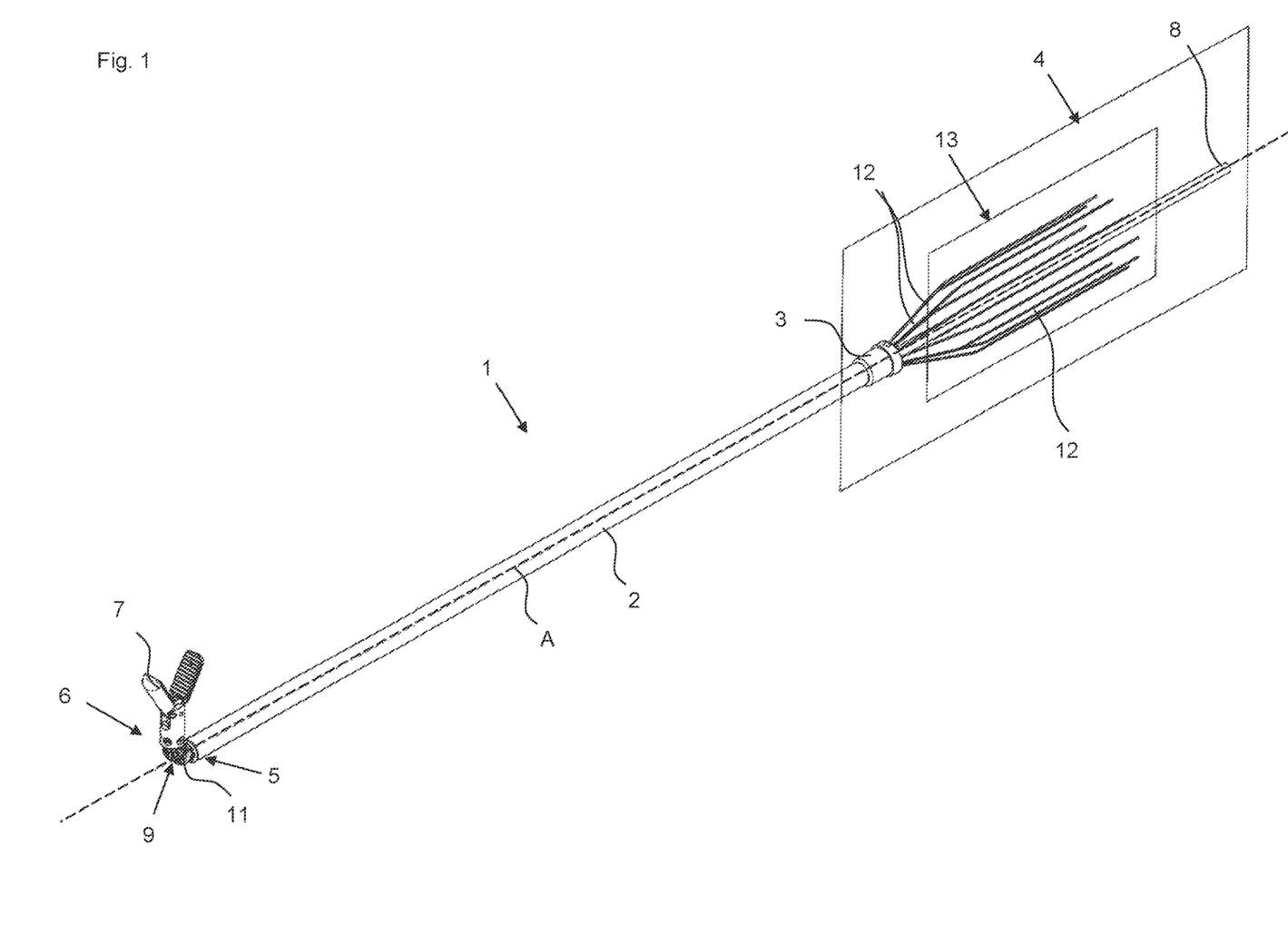
FIG. 1 a schematic perspective side view of a surgical instrument according to one exemplary embodiment, FIG. 2 a schematic sectional side view of an embodiment of a locking device according to an exemplary embodiment in a) locking position, b) release position and c) an alternative locking position, FIG. 3 a schematic sectional side view of a further embodiment of a locking device according to an exemplary embodiment in a) locking position and b) release position and c) release position with the instrument insert moved axially in the distal direction, FIG. 4 a perspective sectional detail view of a further embodiment of a locking device according to an exemplary embodiment in the locking position, FIG. 5 a perspective view of a cam wheel as an actuation device of a locking device according to an exemplary embodiment, FIG. 6 a perspective sectional view of the locking device from FIG. 4 with the actuation device from FIG. 5, FIG. 7 a schematic side sectional view of a further embodiment of a locking device according to an exemplary embodiment in a) locking position and b) release position, FIG. 8 a schematic side sectional view of a further embodiment of a locking device in a) locking position and b) release position.

FIG. 1 schematically shows a surgical instrument 1 with a hollow shaft 2, an actuation unit 4, illustrated only schematically, arranged at the proximal end 3 of the shaft 2 and with an instrument tip 6 arranged at the distal end 5 of the shaft 2 with a tool 7, which is designed here as a gripping tool and can be pivoted relative to the longitudinal axis A of the shaft 2 via a joint mechanism 9 made of pivoting members 11. For this purpose, an actuating mechanism, not described here, can be provided via guide wires 12 which are actuated by a drive 13 arranged at the proximal end 3 of the shaft 2 in the actuation unit 4.

As an alternative to the gripping tool shown, the tool 7 of the instrument tip 6 can be an endoscope, an applicator or the like. To operate the tool 7, e.g., for opening and closing gripping elements, the tool 7 is operatively connected to the actuation unit 4 on the proximal side via an instrument insert 8 mounted in the shaft 2, so that it can be displaced axially in the direction of the longitudinal axis A. To actuate the tool 7, the instrument insert 8, which is mounted axially displaceable in the shaft 2, is designed as a push/pull rod in the examples shown and is referred to below as a pull rod 8, without this limiting the scope of protection. The term "pull rod" should be understood as representing all axially displaceable instrument inserts.

The actuation unit 4 can preferably be designed for robotic application and thus be a structural unit that can also be actuated without manual intervention—which is advantageous for the reproducibility of the actuation. In addition to the motors for pivoting the tool tip by means of guide wires, the drive 13 can therefore have further motors for a linear movement and for a rotary movement of the pull rod 8 in order to enable further functions or mechanisms of the tool 7, such as actuating the opening and closing of gripping elements.

Thus, while using the surgical instrument 1, the fixing and subsequent release of the tool 7, e.g., the gripping elements, may be desirable, for example to achieve exact positioning or to exert a constant gripping force. According to the an exemplary embodiment, a locking device 10 is proposed for this purpose in FIGS. 2 to 4. Examples are illustrated. This locking device 10 is intended to be arranged in the proximal actuation unit 4 and has an engaging element for engaging with the pull rod 8 and an actuation device for the engaging element to move the engaging element from a release position in which there is no engagement with the pull rod 8, and its axial movement can be transferred to a locking position and vice versa, in which the engaging element is engaged with the tie rod 8, so that axial movement of the pull rod is prevented. However, a rotational movement of the pull rod 8 for actuating another tool mechanism can also be permitted in the locking position.

Figure 2:
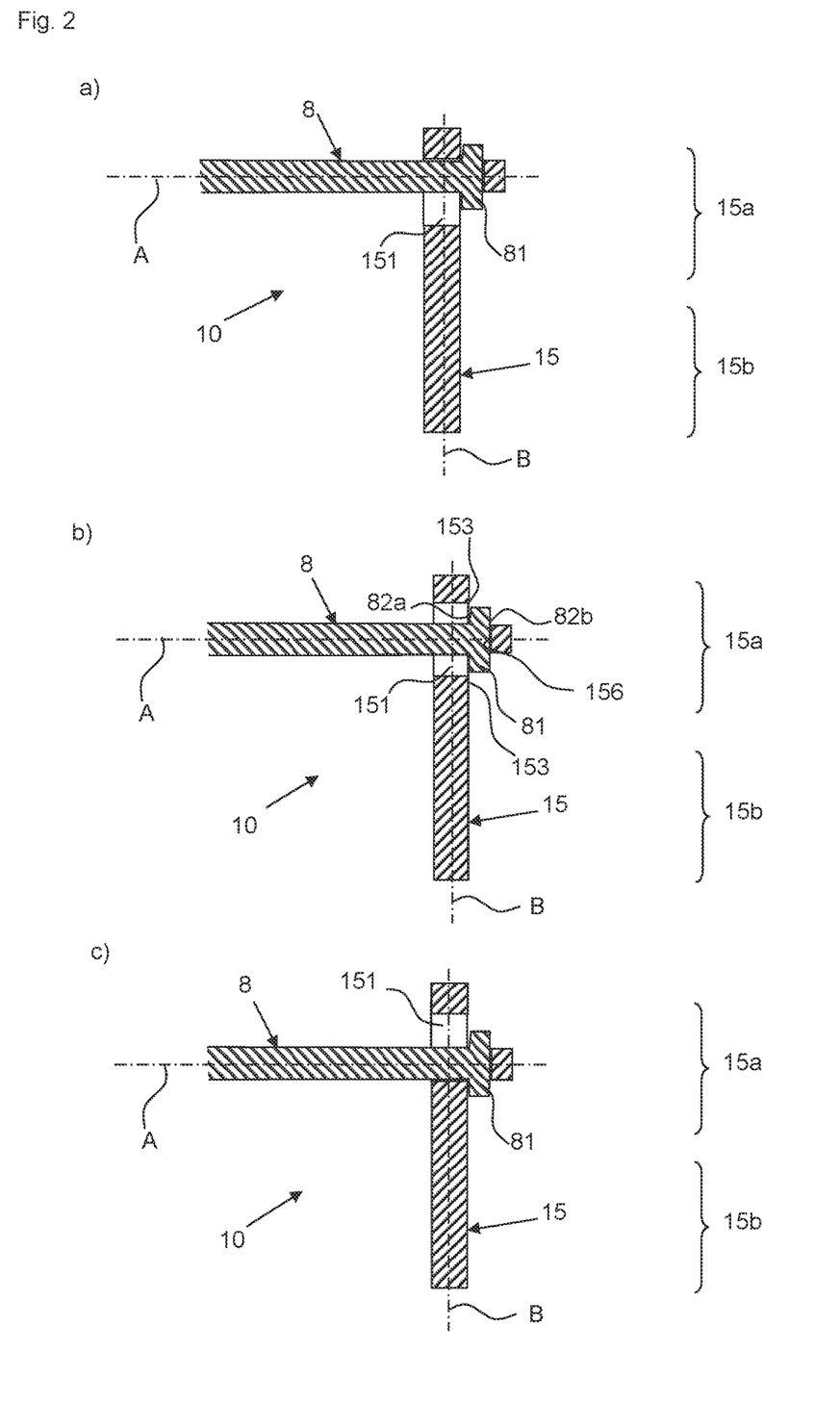
Figure 3:
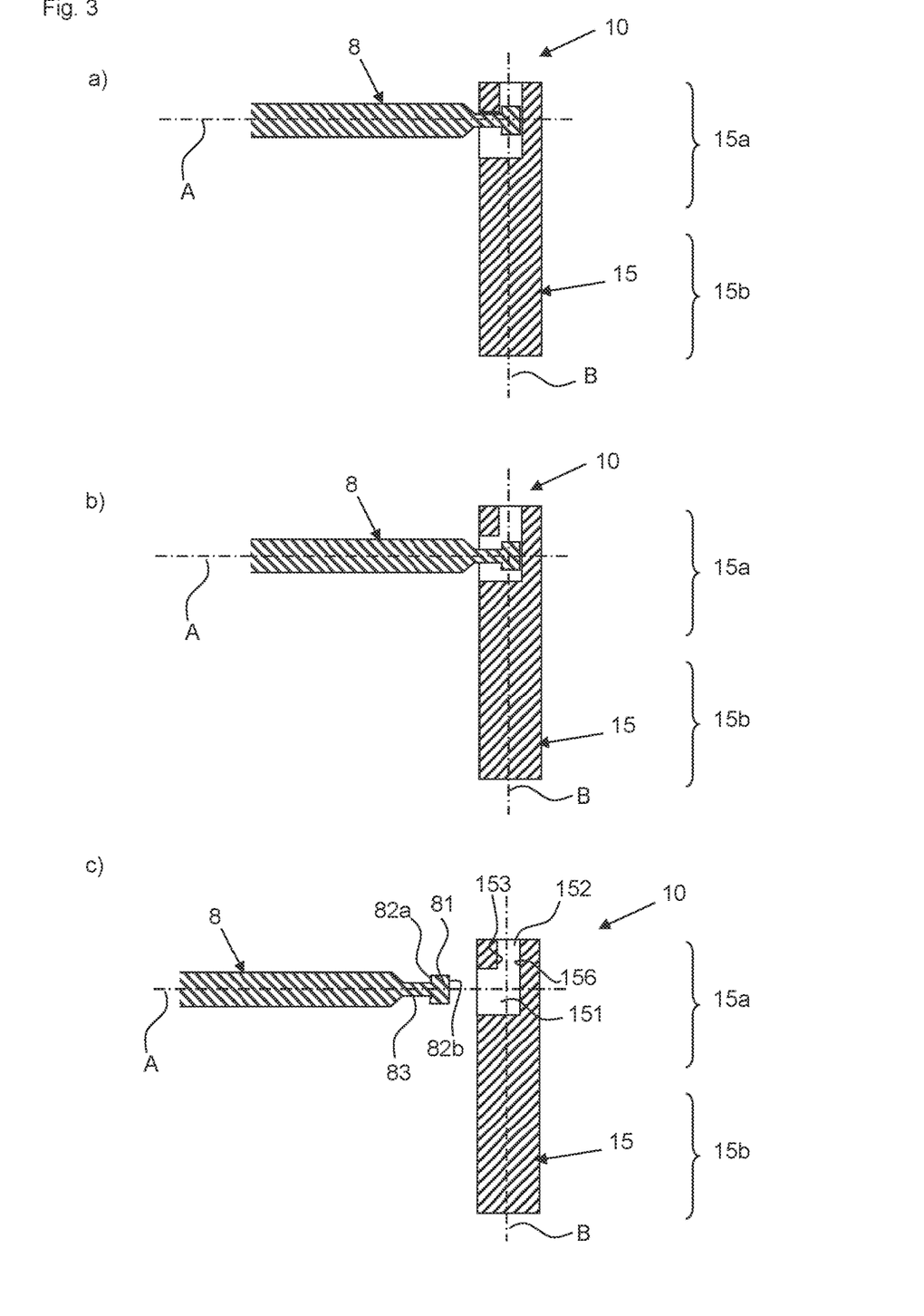
Figure 6:
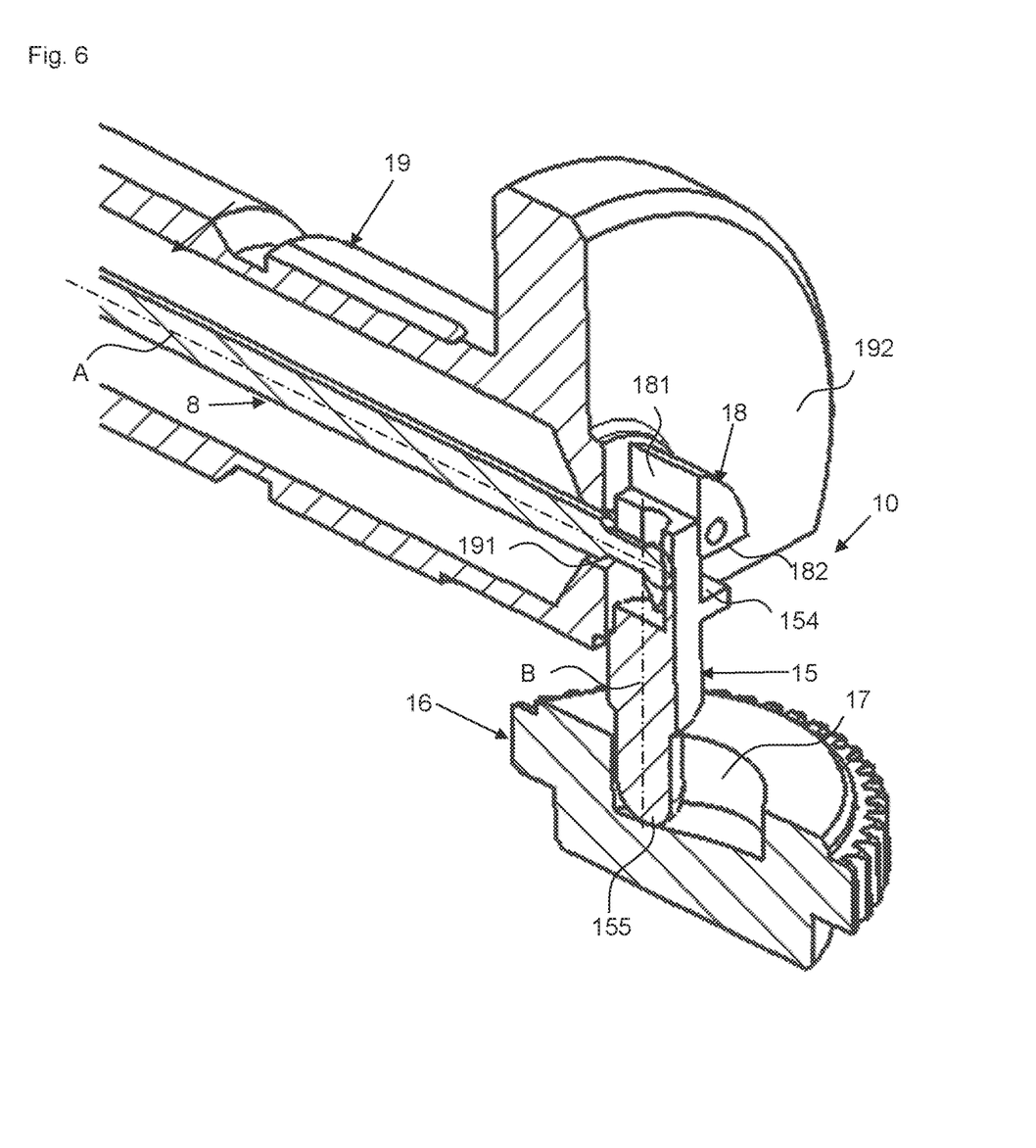
Figure 7:
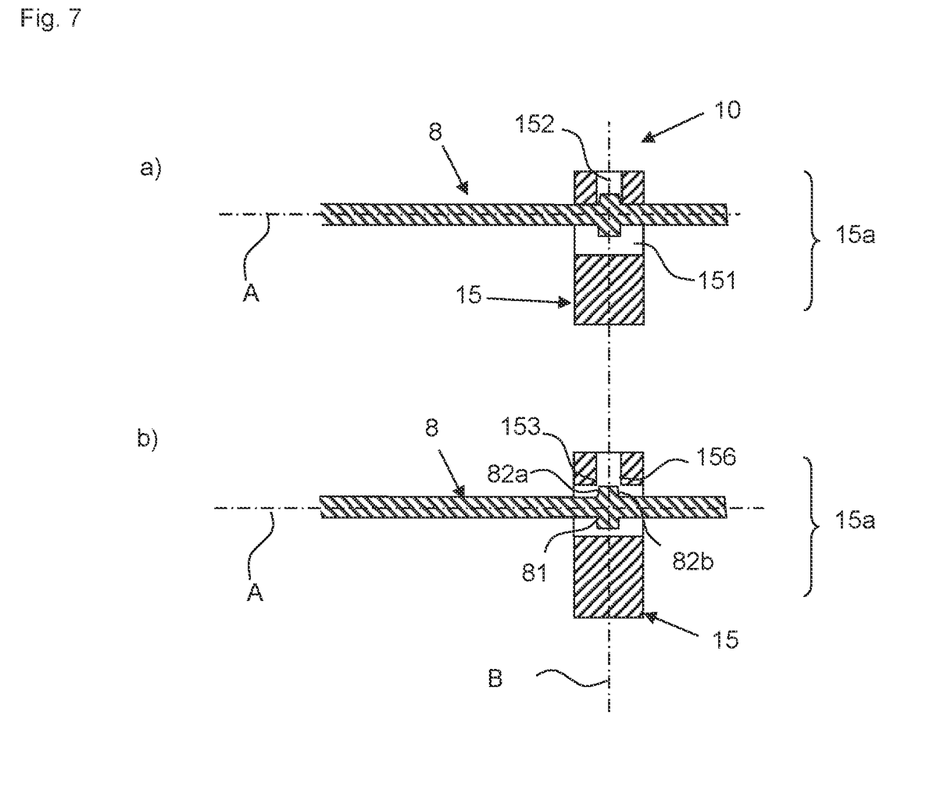

In the locking device according to an exemplary embodiment, the engagement element is a locking bolt 15, for which a first embodiment is shown in FIG. 2 and a second embodiment in FIGS. 3, 4, 6 and 8 and a third embodiment in FIG. 7. The schematic representations in FIGS. 2, 3 and 7 illustrate the locking and release position of the pull rod 8 on the engagement section 15a of the locking bolt 15, while the guide section 15b is not defined there. The locking bolt 15 is arranged with its longitudinal axis B perpendicular to the main instrument axis A and thus perpendicular to the pull rod 8 in the examples of FIGS. 2, 3, 4, 6 and 8. At its proximal end it has a detached head section 81 which provides a distal-side axial bearing surface 82a and a proximal-side axial contact surface 82b. FIG. 7 shows an embodiment of the locking device 10 in which the detached section 81 with the distal-side axial contact surface 82a and the proximal-side axial contact surface 82b is not formed on the proximal end of the pull rod 8, but in the area adjacent to the proximal end. In order to form the step that provides the distal-side axial contact surface 82a on the detached section or head section 81, the detached section or head section 81 can be used as shown in FIGS. 2 and 7 and have a rotationally symmetrical cross-sectional area that is larger than the cross-sectional area of the rest of the pull rod 8. Alternatively, as in FIGS. 3, 4, 6 and 8 to form the step that provides the distal-side axial contact surface 82a, a neck section 83 can be provided between the head section 81 and the rest of the pull rod 8, the cross-sectional area of which is smaller than that of the head section 81 and the rest of the pull rod 8. Correspondingly (not shown figuratively), a detached section that is not formed at the proximal end may be detached by two neck sections. The detached (head) section 81 can be cylindrically formed as in the examples of FIGS. 2, 3, 7 and 8, or almost spherical as in FIGS. 4 and 6.

For engagement with the pull rod 8 or the detached section/head section 81 of the pull rod 8, the locking bolt 15 has a receiving bore 151 on the engagement section 15a, which bore extends perpendicularly to the longitudinal axis B of the locking bolt 15 in the direction of the main instrument axis A or parallel thereto. The receiving bore 151 is dimensioned to receive the detached section/head section 81 so that it can be moved in and out of the receiving bore 151 in the direction of the main axis A of the instrument without any problems. To transfer the locking bolt 15 between a release position, in which the pull rod 8 is axially movable, and a locking position, in which the locking bolt 15 engages with the pull rod 8, the locking bolt 15 is moved along its longitudinal axis B perpendicular to the main axis A of the instrument.

The engagement of the locking bolt 15 with the pull rod 8 is provided in that the detached section/head section 81 engages behind the receiving bore 151 in the locking bolt 15 after this has been transferred along its longitudinal axis B into the locking position. Due to a rotationally symmetrical shape of the detached section/head section 81, this rear grip is retained even when the pull rod 8 rotates.

In the example of FIG. 2 the receiving bore 151 is a through-bore, for which, as can be seen in the release position in FIG. 2b, distal counter-contact surfaces 153 above and below the receiving bore 151 on the proximal outer side of the locking bolt 15 border on which the distal-side axial contact surface 82a on the head section 81 of the pull rod 8 can rest. Optionally and depending on the direction in which locking bolt 15 is actuated, the head section 81 engages behind it in the locking position by contact of the distal-side axial contact surface 82a on the distal counter-contact surface 153 above or below the receiving bore 151, as in FIGS. 2a and c, which is shown to prevent axial movement of the pull rod 8 in the distal direction. If the locking bolt 15, starting from the release position in FIG. 2b, is moved downwards for transfer into the locking position, the head section 81 rests on the distal counter-contact surface 153 above the receiving bore 151, as in FIG. 2a shown. As an alternative to this, the locking bolt 15 is transferred from the release position to FIG. 2b up to a locking position FIG. 2c, in which the head section 81 bears against the distal counter-contact surface 153 below the receiving bore 151. In both cases, the axial movement of the pull rod 8 in the proximal direction is prevented by a proximal counter-contact surface 156 of the locking device 10. The proximal counter-contact surface 156, on which the proximal-side axial contact surface 82b of the head section 81 comes to rest, is shown in the example of FIG. 2 provided by a component that is separate from the locking bolt 15 and that is arranged at the level of the main instrument axis A and spaced from the distal contact surface 153 by the length of the head section 81. Modifications of this embodiment for a pull rod that are not shown, in which the detached section is not formed at the proximal end, but rather at a distance from it in a proximal end region, provide that the proximal counter-contact surface be designed differently than shown, e.g., can be provided by an annular component, so that the end section of the pull rod can extend through an opening aligned with the receiving bore. As an alternative to this, the component that provides the proximal counter-contact surface can be arranged detached parallel to the main axis A of the instrument with respect to the distal counter-contact surface 153.

Figure 4:
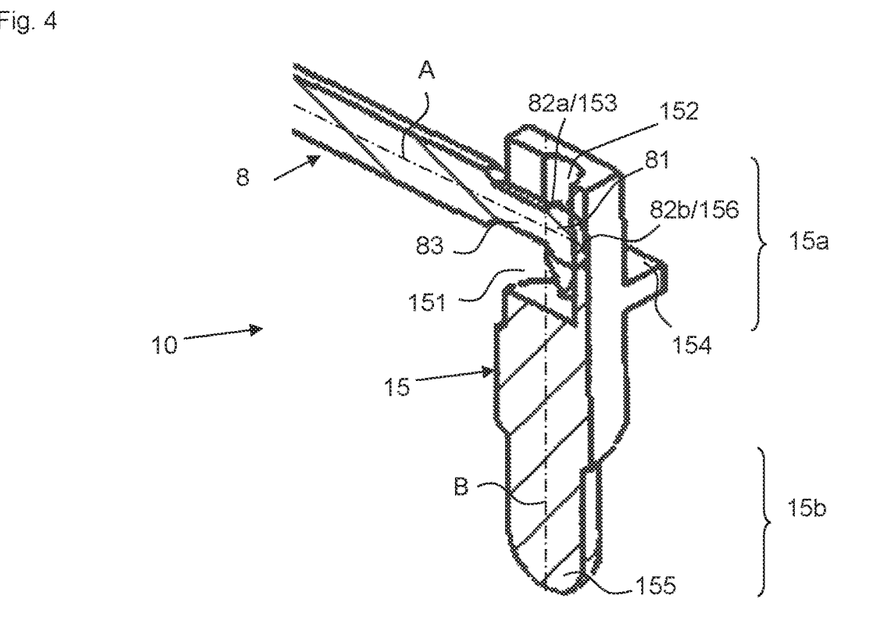

FIG. 3 illustrates the function of the locking device 10, which is also shown in FIGS. 4 and 6. In contrast to FIG. 2, here, the receiving bore 151 is not a through-bore but a blind bore, with the distal counter-contact surface 153 being provided by an engagement bore 152, which extends perpendicularly to the receiving bore 151 approximately along the longitudinal axis B of the locking bolt 15 to the receiving bore 151. FIG. 3a (and also FIGS. 4 and 6) show the locking device 10 in the locking position of the locking bolt 15, in which the head section 81 of the pull rod 8 rests with the distal-side contact surface 82a on the distal counter-contact surface 153 above the receiving bore 151, whereby an axial movement of the pull rod 8 in the distal direction is prevented. The proximal contact surface 156 for preventing the pull rod 8 from moving axially in the proximal direction is provided by a proximal wall (borehole base) of the receiving bore 151 designed as a blind hole or by a proximal wall of the engagement bore 152, which adjoins the bore base of the receiving bore designed as a blind bore 151. For transfer to the release position in FIG. 3b starting from the locking position, the locking bolt 15 in FIG. 3a is moved upwards (compare FIG. 8) so that the head section 81 of the pull rod 8 is completely in the receiving bore 151 and the pull rod 8 can thus be moved axially along the main instrument axis A, as in FIG. 3c to operate a distal tool mechanism or to replace the pull rod 8.

Not shown figuratively, but nevertheless according to an exemplary embodiment, is an embodiment in which the engagement bore 152 extends beyond the receiving bore 151, so that a further distal counter-contact surface 153 and proximal counter-contact surface 156 are created below the receiving bore 151. As in the example of FIG. 2, an alternative locking position can be optionally set, in which the head section 81 of the pull rod 8 comes to rest with the distal-side and proximal-side contact surface 82a, 82b on a distal and proximal counter-contact surface below the receiving bore 151. Furthermore, the use of differently designed tie rods is not limited to the example shown in each case. A locking device according to an exemplary embodiment can thus correspond to a locking bolt with a through hole FIG. 2 for engagement with a pull rod, in which the head section as in FIG. 3 is separated by a neck section. A locking device according to the an exemplary embodiment can also correspond to a locking bolt with a blind hole and an engagement hole FIG. 3 for engagement with a pull rod, in which the head section as in FIG. 2 is deposed by a cross-sectional enlargement.

Corresponding modifications are also possible for conceivable embodiment illustrated in FIG. 7, which shows a locking device 10 with a detached section 81 which is not formed at the proximal end of the pull rod 8. In this case, the receiving bore 151 in the locking bolt 15 is a through-bore into which the engagement bore 152 opens in order to provide the distal and proximal counter-contact surfaces 153, 156 adjacent to the receiving bore 151 for engagement with the detached section in the locking position of the locking bolt 15 (FIG. 7a). Starting from this locking position, the locking bolt 15 is moved upwards to the release position in FIG. 7b, so that the mounting hole 151 is aligned with the main axis A of the instrument and the detached section 81 of the pull rod 8 is completely in the mounting hole 151 and the pull rod 8 can thus be moved axially along the main axis A of the instrument.

Figure 5:
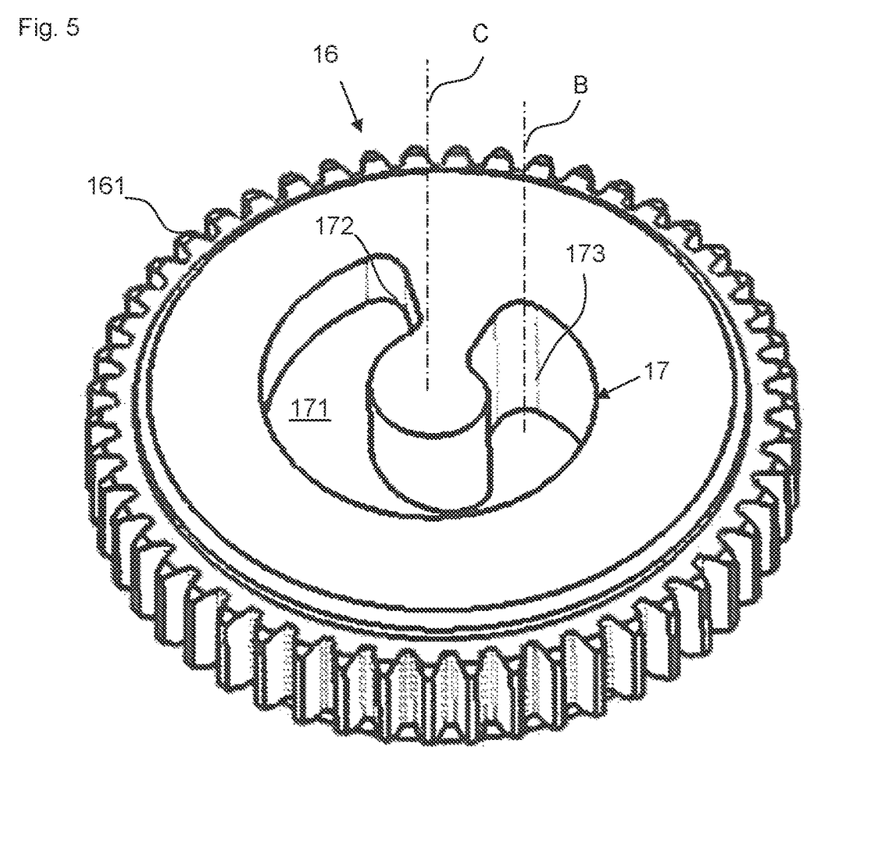

In FIG. 4 a locking device 10, which essentially corresponds to FIG. 3, is shown in more detail, while the technical interaction with other components, such as the actuation device designed as a cam wheel 16, which is illustrated separately in FIG. 5, is shown in FIG. 6. Therefore, FIG. 4 shows, at the engagement section 15a, a flattened outer section extending from the upper end to a ridge providing a stop surface 154 of the locking bolt 15 extending perpendicularly to the longitudinal axis B. With this stop surface 154, the locking bolt 15 comes to rest in the release position against a stop 182, which in the example of FIG. 6 is formed on a guide element 18. This serves to ensure that the pull rod 8 can only be removed when the locking bolt 8 has moved to the stop. In the example shown, the guide element 18 is also designed to guide the locking bolt 15 and for this purpose it provides a guide surface 181 parallel to the longitudinal axis B of the locking bolt 15 and perpendicular to the stop 182, so that the flattened outer section of the locking bolt 15 can be guided on the guide surface 181. In the example shown, the guide element 18 is arranged on the proximal end face 192 of a housing component 19, through which the pull rod 8 extends, with the pull rod 8 extending at least with the head section 81 for engagement with the locking bolt 15 through a passage opening 191 in the proximal end face 192 extending out of the housing component 19. For a symmetrical guide and stop on both sides, corresponding guide element 18 with guide surface 181 and stop 182 as well as a flattened outer section and stop surface 152 on the locking bolt 15 can be formed on both sides. Of course, different designs and arrangements of stop and guide elements are conceivable.

The actuation device of a locking device according to the an exemplary embodiment is described in more detail below using an example, in which the actuation device is a horizontally arranged cam wheel 16 with a cam track 17 for guiding the locking bolt 15, which longitudinal axis B extends in the plumb direction, i.e., vertically, so that the movement along the longitudinal axis B for locking and releasing the pull rod is an up and down movement.

Figure 8:
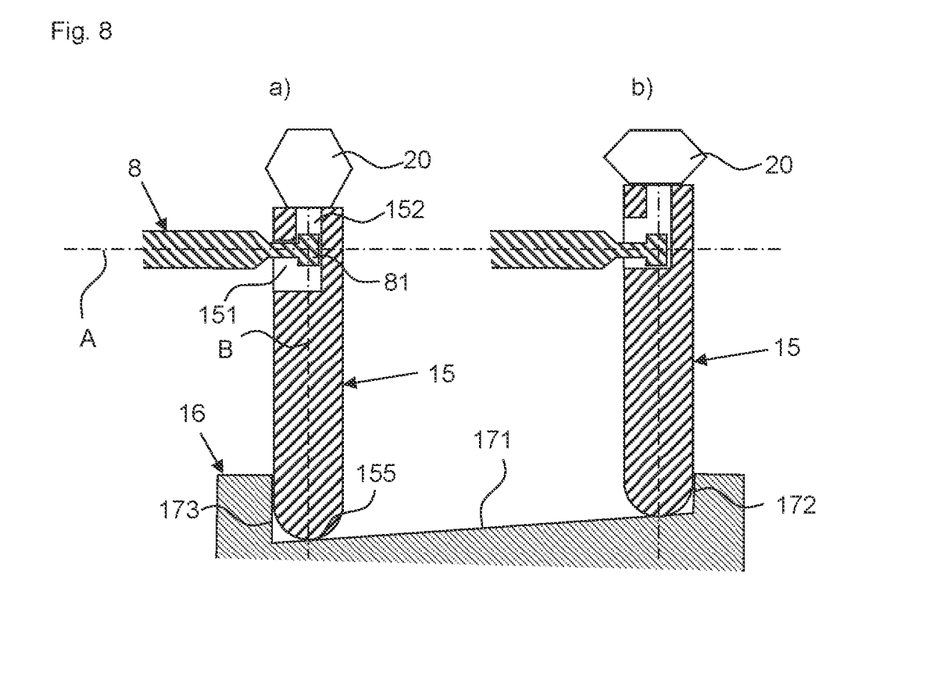

FIG. 4 shows the guide section 15b of the locking bolt 15 with a rounded end 155 to ensure low-friction guidance in the support of the cam track 17 of the cam wheel 16 (compare FIGS. 5, 6 and 8). The diameter of the locking bolt 15 on the guide section 15b can be smaller than on the rest of the locking bolt 15 in order to be guided in the cam track 17 with almost no play. In order to move the locking bolt 15 up and down along its longitudinal axis B, the cam track 17 extends in the shape of a circular arc with a constant radius around the axis of rotation C of the cam wheel 16 with a bottom 171 inclined between a first, upper end stop 172 and a second, lower end stop 173. In the example shown in FIG. 5 the depth of the cam track 17 thus increases anticlockwise. If the locking bolt 15 rests with its guide section 15b on the second, lower end stop 173, as indicated in FIG. 5, drawn longitudinal axis B indicated, the locking bolt 15 is in relation to the plumb direction lower end position, which corresponds to the locking position in the example illustrated in FIGS. 4 and 6. In order to transfer the locking bolt 15 from the locking position to the release position, the locking bolt 15 is moved upwards by the cam wheel 16 of the example shown in FIG. 5 and is rotated anticlockwise, so that the guided locking bolt 15 on the bottom 171 of the cam track 17 is raised following the slope of the bottom 171 to the upper end stop 172. To return to the locking position—e.g., after repositioning of the distal tool 7—the cam wheel 16 is turned clockwise so that the locking bolt 15 is lowered from the upper end stop 172 under the force of gravity along the inclined bottom 171 to the lower end stop 173 along its longitudinal axis B again. If, in an alternative embodiment, the slope of the bottom of a cam track is reversed, i.e., the depth of the cam track increases clockwise, the cam wheel for transferring the illustrated locking bolt 15 from the locking position is correspondingly reversed i.e., rotated clockwise so that the locking bolt 15 is moved upwards to the release position. Correspondingly, the cam wheel has to be turned anticlockwise so that the locking bolt is transferred downwards from the release position to the locking position.

In order to move the cam wheel 16 by means of a motor (not illustrated), the cam wheel 16 in the illustrated example has a ring gear 161 in which a pinion (also not illustrated) can engage, which is driven by a motor. Of course, alternative drive variants, e.g., conceivable via traction pulleys etc., and the drive ring do not have to extend over the entire circumference, but only over a section corresponding to the length of the cam track.

FIG. 8 shows the cam track 17 of the cam wheel 16 in a development in the plane of representation, from which the slope of the bottom 171 between the lower end stop 173 and the upper end stop 172 is particularly clearly visible. The representation of a locking bolt 15 at the upper and lower end stop 172, 173 serves only to clarify and compare the locking position provided in a) and the release position in b), between which the locking bolt 15 is guided in the cam track 17 with the rounded end 155 and can be transferred to the bottom 171 by appropriate rotation of the cam wheel 16. In FIG. 8 a fuse element 20 is also shown, which holds the locking bolt 15 on the bottom 171 of the cam track 17 by the fuse element 20 acting on the locking bolt 15 with a restoring force in the direction of the longitudinal axis B. Alternatively, as a fuse element, lateral projections on the guide section of the locking bolt can engage in lateral guide grooves on the cam track parallel to the bottom or vice versa (rails on the cam track in grooves in the locking bolt) in order to hold the locking bolt on the bottom of the guide groove.

The examples described should not be construed as limiting the invention with respect to the direction of rotation of the cam wheel for up and down movement of the indexing bolt and with respect to the direction of movement of the indexing bolt for locking and releasing. These can be varied in any combination within the scope of protection. Furthermore, the invention should not be limited to the vertical arrangement of the locking bolt, even if this embodiment is particularly advantageous, since gravity ensures that the locking bolt remains on the bottom of the cam track, and additional securing and retaining elements can therefore be dispensed with as is required when the locking bolt is arranged in a manner that deviates from the plumb direction, in order to keep the locking bolt on the bottom of the cam track.

LIST OF REFERENCE NUMBERS

1 Surgical instrument
2 Shaft
3, 5 Proximal, distal end (shaft)
4 Actuation unit 6 Instrument tip
7 Tool
8 Instrument insert/pull rod
81, 82a/b, 83 Detached (head) section, distal/proximal contact surface, neck section
9 Joint mechanism
10 Locking device
11 Swivel link
12 Guide wire
13 Drive
15 Locking bolt
15A, 15b Engagement section, guide section
151, 152 Receiving bore, engagement bore
153, 156 Distal, proximal counter-contact surface
154 Stop surface
155 Rounding off
16 Cam wheel
161 Ring gear
17 Cam track
171 Bottom
172, 173 First (upper) end stop, second (lower) end stop
18 Guide element
181, 182 Guide surface, stop
19 Housing component
191, 192 Passage opening, proximal front face
20 Fuse element
A Main instrument axis
B Axis of movement locking bolt
C Axis of rotation cam wheel

The invention claimed is:

1. An apparatus comprising:
a surgical instrument, and
a locking device configured for arrangement in an actuation unit of the surgical instrument, the surgical instrument including a hollow shaft with the actuation unit arranged at a proximal end of the shaft and having a tool at a distal end of the shaft, which can be actuated by an instrument insert which is configured to be movably stored axially in a direction of a main axis of the surgical instrument in the shaft,
wherein the locking device includes an engagement element configured for engagement with the instrument insert, and the actuation unit which is configured to move the engagement element from a release position, in which there is no engagement with the instrument insert, into a locking position in which the engagement element is in engagement with the instrument insert, wherein:
the engagement element is a locking bolt with a longitudinal axis that runs perpendicular to the main axis of the surgical instrument and which has an engagement section configured for engagement with the instrument insert at a first end and a guide section at a second end which is in operative connection with the actuation unit,
the locking bolt is transferable by the actuation unit in a first direction of movement along the longitudinal axis of the locking bolt perpendicular to the main axis of the surgical instrument from the release position to the locking position and in a second direction of movement, opposite to the first direction of movement, along the longitudinal axis of the locking bolt perpendicular to the main axis of the surgical instrument from the locking position to the release position,
the actuation unit is a cam wheel with a cam track which extends in a shape of a circular arc around an axis of rotation of the cam wheel between a first end stop and a second end stop, and a depth of the cam track increases from the first end stop to the second end stop, so that a bottom of the cam track runs inclined between the first end stop and the second end stop,
and the locking bolt is configured to be guided with the guide section of the locking bolt in the cam track, and the longitudinal axis of the locking bolt is parallel to the axis of rotation of the cam wheel.

2. The apparatus of claim 1, wherein
the longitudinal axis of the locking bolt lies in a vertical direction, and the first end stop is an upper end stop with respect to the vertical direction and the second end stop is a lower end stop with respect to the vertical direction, and/or
the locking device has an element which, regardless of an orientation of the longitudinal axis of the locking bolt in relation to the plumb direction, holds the guide section of the locking bolt on a base of the cam track.

3. The apparatus of claim 1, wherein,
the instrument insert has a detached section, which provides a distal-side axial contact surface and a proximal-side axial contact surface and is a detached head section at a proximal end of the instrument insert,
and the locking bolt has a receiving bore on the engagement section, which extends perpendicularly to the longitudinal axis of the locking bolt and is dimensioned for receiving the detached section, the locking device has a distal counter-contact surface for the distal-side axial contact surface of the detached section and a proximal counter-contact surface for the proximal-side axial contact surface of the detached section, wherein at least the distal-side axial contact surface adjoins the receiving bore in the direction of the longitudinal axis of the locking bolt.

4. The apparatus of claim 3, wherein the receiving bore is a through bore, wherein
the distal counter-contact surface for the distal-side axial contact surface is present on a proximal outer surface of the locking bolt, and
the proximal counter-contact surface for the proximal-side axial contact surface is provided by a separate component which is arranged proximally to the proximal outer surface of the locking bolt.

5. The apparatus of claim 3, wherein
the distal counter-contact surface and the proximal counter-contact surface of the locking bolt are provided by an engagement bore which extends perpendicular to the receiving bore and parallel to or along the longitudinal axis of the locking bolt extending at least up to the receiving bore, the receiving bore being a through bore or a blind bore.

6. The apparatus of claim 1, wherein, the locking device has at least one guide element which has a guide surface parallel to the longitudinal axis of the locking bolt configured to guide the locking bolt along the longitudinal axis of the locking bolt and perpendicular to the main axis of the surgical instrument, wherein the at least one guide element is arranged on a housing component through which the instrument insert extends.

7. The apparatus of claim 1, wherein,
the locking device provides a stop for a stop surface of the locking bolt which extends perpendicularly to the longitudinal axis of the locking bolt, the stop in relation to the instrument insert is positioned in such a way that the locking bolt is in the release position when the stop surface rests against the stop.

8. The apparatus of claim 1, wherein,
the cam wheel has, at least along a predetermined circumferential section, a drive ring which is operatively connected to a drive element driven by a motor.

9. The apparatus of claim 8, wherein
the drive ring is a ring gear and the drive element engaged therewith is a pinion, or
the drive ring and the drive element are formed by traction pulleys that are operatively connected.

10. An apparatus comprising:
a surgical instrument, and
a locking device, the locking device configured for placement in an actuation unit of the surgical instrument, the surgical instrument including a hollow shaft with the actuation unit arranged at a proximal end of the shaft and having a tool at a distal end of the shaft, which can be actuated by an instrument insert which is configured to be movably stored axially in a direction of a main axis of the surgical instrument in the shaft,
wherein the locking device includes:
an engagement element configured for engagement with the instrument insert, and
the actuation unit which is configured to move the engagement element from a release position, in which there is no engagement with the instrument insert, into a locked position in which the engagement element is engaged with the instrument insert,
wherein:
the engagement element is a locking bolt, the locking bolt having a longitudinal axis running perpendicular to the main axis of the surgical instrument, the locking bolt also having an engagement section configured for engagement with the instrument insert at a first end, and a guide section at a second end, wherein the guide section is in operative connection with the actuation unit,
the locking bolt is moveable by the actuation unit in a first direction of movement along the longitudinal axis of the locking bolt perpendicular to the main axis of the surgical instrument from the release position to the locked position, and in a second direction of movement, opposite to the first direction of movement, along the longitudinal axis of the locking bolt perpendicular to the main axis of the surgical instrument from the locked position to the release position,
the actuation unit is a cam wheel including a cam track which extends in a circular arc around an axis of rotation of the cam wheel between a first end stop and a second end stop, and a depth of the cam track increases from the first end stop to the second end stop, so that a bottom of the cam track is inclined between the first end stop and the second end stop, and
the locking bolt is configured to be guided with the guide section of the locking bolt in the cam track, and the longitudinal axis of the locking bolt is parallel to the axis of rotation of the cam wheel.

* * * * *